(12) United States Patent
Johnson et al.

(10) Patent No.: US 11,331,155 B2
(45) Date of Patent: May 17, 2022

(54) CONSISTENT AND REPEATABLE JAW GAP FOR SURGICAL TOOL END EFFECTOR

(71) Applicant: Ethicon LLC, Guaynabo, PR (US)

(72) Inventors: Eric N. Johnson, Maineville, OH (US); Mark Allen Davison, Maineville, OH (US)

(73) Assignee: Ethicon LLC, Guaynabo, PR (US)

( * ) Notice: Subject to any disclaimer, the term of this patent is extended or adjusted under 35 U.S.C. 154(b) by 101 days.

(21) Appl. No.: 16/549,183

(22) Filed: Aug. 23, 2019

(65) Prior Publication Data
US 2021/0052334 A1 Feb. 25, 2021

(51) Int. Cl.
*A61B 34/30* (2016.01)
*A61B 17/29* (2006.01)
*A61B 18/14* (2006.01)
*A61B 17/00* (2006.01)

(52) U.S. Cl.
CPC ........ *A61B 34/30* (2016.02); *A61B 17/00234* (2013.01); *A61B 17/29* (2013.01); *A61B 18/1442* (2013.01); *A61B 2017/0046* (2013.01); *A61B 2017/00398* (2013.01); *A61B 2017/00477* (2013.01); *A61B 2017/2926* (2013.01); *A61B 2034/305* (2016.02)

(58) Field of Classification Search
CPC ..... A61B 34/30; A61B 17/29; A61B 18/1442; A61B 17/00234; A61B 2017/2926; A61B 2017/00398; A61B 2034/305; A61B 2017/0046; A61B 2017/00477; A61B 17/2816; A61B 17/282; A61B 2017/2825; A61B 2017/2947; A61B 17/295; A61B 18/1445; A61B 2018/145; A61B 2018/1452; A61B 2018/1455; A61B 2018/1457
See application file for complete search history.

(56) References Cited

U.S. PATENT DOCUMENTS

| 2016/0074099 | A1* | 3/2016 | Kappus | A61B 18/1445 29/434 |
|---|---|---|---|---|
| 2017/0312017 | A1* | 11/2017 | Trees | A61B 18/1442 |
| 2018/0125569 | A1* | 5/2018 | Vaders | B29C 70/76 |
| 2018/0126149 | A1* | 5/2018 | Vaders | A61B 18/1445 |

* cited by examiner

*Primary Examiner* — Kelly J Bekker
*Assistant Examiner* — Mohammed S Adam
(74) *Attorney, Agent, or Firm* — Vorys, Sater, Seymour and Pease LLP (57) ABSTRACT

An end effector for a surgical tool includes a first jaw that defines an aperture, a second jaw rotatably coupled to the first jaw, and a spacer pin received within the aperture and protruding from an upper surface of the first jaw. The spacer pin is adjustable within the aperture to define a jaw gap between the first and second jaws when the second jaw is moved to a closed position and engages the spacer pin, and the spacer pin is secured within the aperture to set the jaw gap.

23 Claims, 6 Drawing Sheets

CONSISTENT AND REPEATABLE JAW GAP FOR SURGICAL TOOL END EFFECTOR

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables (or other elongate members) that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system and thereby actively controlling the tension balance in the drive cables. Moving the drive cables articulates the end effector to desired angular positions and configurations.

Some end effectors have actuatable opposing jaws designed to undertake various operations during use. One type of end effector with opposing jaws, for instance, is a combination tissue grasper and vessel sealer with jaws configured to open and close to grasp onto tissue, cut through the tissue, and seal the cut tissue through electrocautery means. The gap between the opposing jaws when fully closed, referred to herein as "jaw gap," is critical to effective operation of the tissue grasper and vessel sealer in creating proper tissue seals. If the jaw gap exceeds predetermined manufacturing tolerances by just a few thousands of an inch, the jaws may be incapable of properly sealing tissue. In such cases, the end effector will be unfit for its intended purpose and may be scrapped as a total loss.

Jaw gap is typically set during manufacture and assembly of the end effector, and has to take into account manufacturing tolerances that are inherent in the individual components of the end effector. What is needed is a method of consistently and accurately setting jaw gap on end effectors with opposing jaws.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, methods and systems for creating a reliable and robust jaw gap between opposing jaws of a surgical tool.

Embodiments described herein disclose systems and methods of setting a jaw gap of an end effector. One example method includes receiving a spacer pin within an aperture defined in a first jaw of the end effector, the spacer pin protruding from an upper surface of the first jaw, and positioning a shim on the upper surface of the first jaw, the shim having a thickness corresponding to the target jaw gap. A second jaw may then be rotatably coupled to the first jaw and pivoted toward a closed position, which proceeds to press the spacer pin into the aperture with the second jaw. The second jaw may be stopped from pressing the spacer pin into the aperture once the second jaw engages the shim, at which point the spacer pin may be secured to the first jaw within the aperture.

Another example method includes positioning a shim on an upper surface of a first jaw, the shim having a thickness corresponding to the jaw gap, and rotatably coupling a second jaw to the first jaw and pivoting the second jaw to a closed position where the second jaw engages the shim. A spacer pin may then be dropped into the aperture and advanced until engaging the second jaw, at which point the spacer pin may be secured to the first jaw within the aperture.

Figure 1:
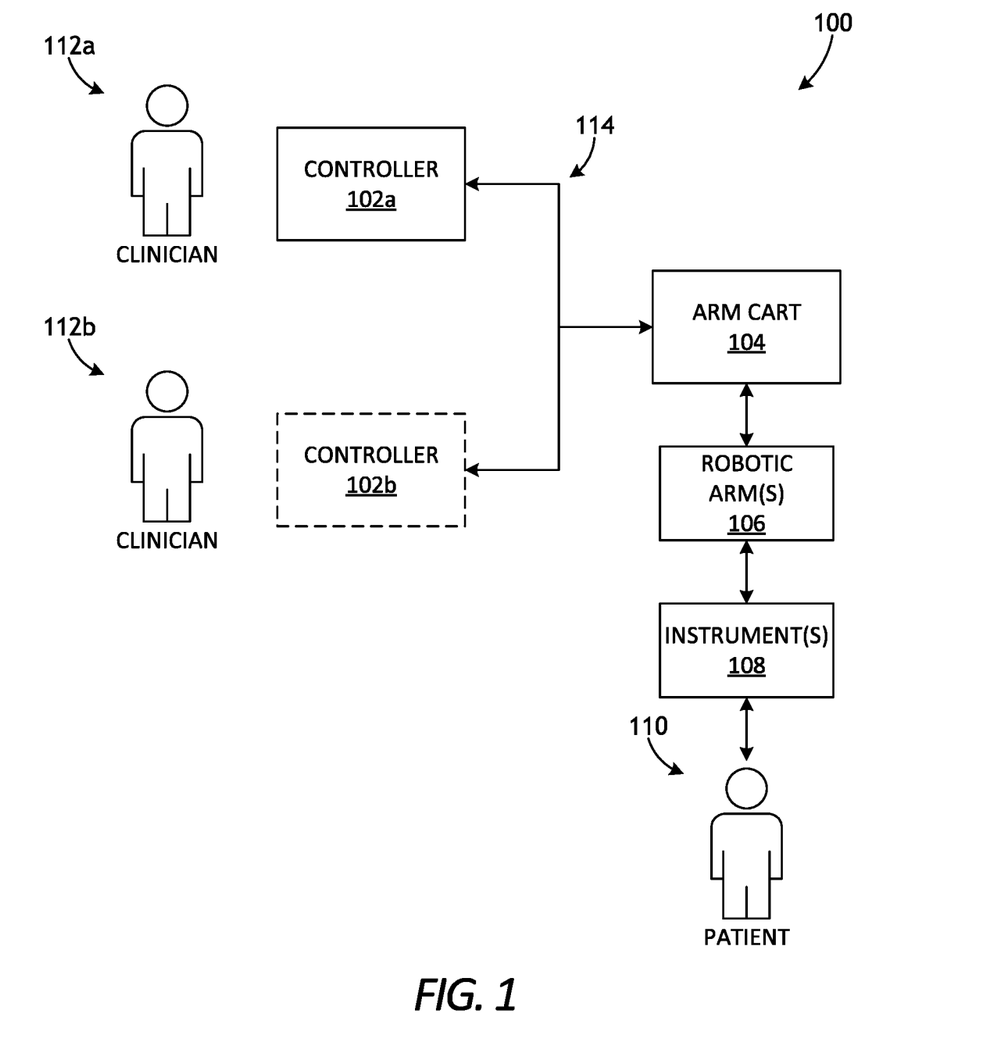
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102a and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112a (e.g., a surgeon) from the user input controller 102a.

In some embodiments, a second set of user input controllers 102b (shown in dashed lines) may be operated by a second clinician 112b to direct operation of the robotic arms 106 and tools 108 in conjunction with the first clinician 112a. In such embodiments, for example, each clinician 112a,b may control different robotic arms 106 or, in some cases, complete control of the robotic arms 106 may be passed between the clinicians 112a,b. In some embodiments, additional robotic manipulators (not shown) having additional robotic arms (not shown) may be utilized during surgery on the patient 110, and these additional robotic arms may be controlled by one or more of the user input controllers 102a,b.

The control computer 104 and the user input controllers 102a,b may be in communication with one another via a communications link 114, which may be any type of wired or wireless telecommunications means configured to carry a variety of communication signals (e.g., electrical, optical, infrared, etc.) and according to any communications protocol.

The user input controllers 102a,b generally include one or more physical controllers that can be grasped by the clinician 112a,b and manipulated in space while viewing the procedure via a stereo display. The physical controllers generally comprise manual input devices movable in multiple degrees of freedom, and often include an actuatable handle or pedal for actuating the surgical tool(s) 108. The control computer 104 can also include an optional feedback meter viewable by the clinician 112a,b via a display to provide a visual indication of various surgical instrument metrics, such as the amount of force being applied to the surgical instrument (i.e., a cutting instrument or dynamic clamping member).

Figures 2, 3:
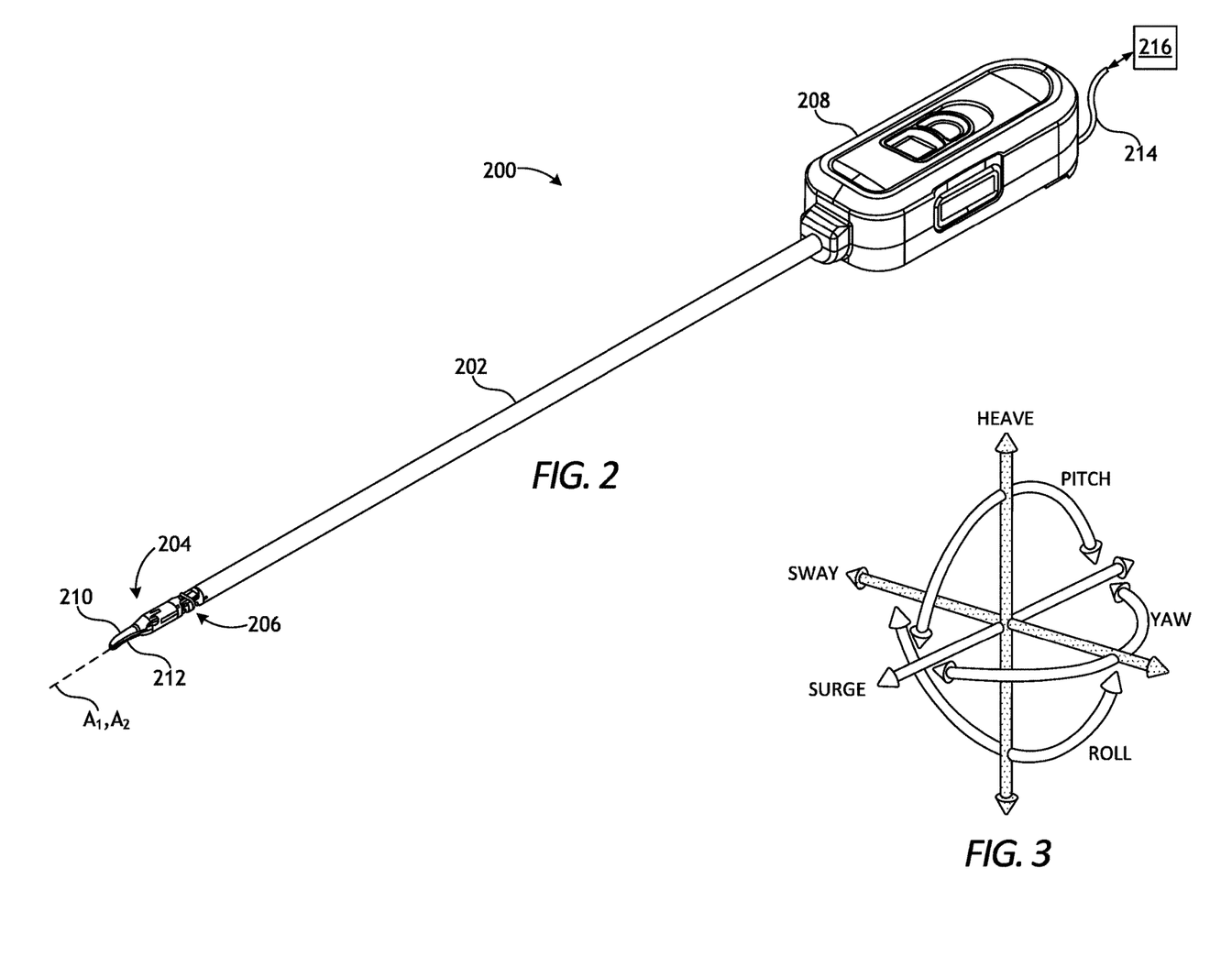
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) or translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In robotic surgical systems, the drive housing 208 can include coupling features that releasably couple the surgical tool 200 to a robotic surgical system (e.g., the robotic arm 106 of FIG. 1).

The terms "proximal" and "distal" are defined herein relative to a robotic surgical system having an interface configured to mechanically and electrically couple the surgical tool 200 (e.g., the drive housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the drive housing 208 includes (contains) various drive inputs and mechanisms (e.g., gears, actuators, etc.) designed to control operation of various features associated with the end effector 204 (e.g., clamping, firing, rotation, articulation, cutting, etc.). In at least some applications, the shaft 202, and hence the end effector 204 coupled thereto, is configured to rotate about a longitudinal axis $A_1$ of the shaft 202. In such embodiments, at least one of the drive inputs controls rotational movement of the shaft 202 about the longitudinal axis $A_1$.

The surgical tool 200 may include, but is not limited to, forceps, a grasper, a needle driver, scissors, an electrocautery tool, a vessel sealer, a stapler, a clip applier, a hook, a spatula, a suction tool, an irrigation tool, an imaging device (e.g., an endoscope or ultrasonic probe), or any combination thereof. In some embodiments, the surgical tool 200 may be configured to apply energy to tissue, such as radio frequency (RF) energy. In the illustrated embodiment, the end effector 204 comprises a tissue grasper and vessel sealer that includes opposing jaws 210, 212 configured to move (articulate) between open and closed positions. As will be appreciated, however, the opposing jaws 210, 212 may alternatively form part of other types of end effectors such as, but not limited to, surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot relative to the other to open and close the jaws 210, 212.

FIG. 3 illustrates the potential degrees of freedom in which the wrist 206 may be able to articulate (pivot). The wrist 206 comprises a joint configured to allow pivoting movement of the end effector 204 relative to the shaft 202. The degrees of freedom of the wrist 206 are represented by three translational variables (i.e., surge, heave, and sway) and three rotational variables (i.e., Euler angles or roll, pitch, and yaw). The translational and rotational variables describe the position and orientation of the end effector 204 with respect to a given reference Cartesian frame. "Surge" refers to forward and backward translational movement, "heave" refers to translational movement up and down, and "sway" refers to translational movement left and right. "Roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system that facilitates movement and articulation of the end effector 204 relative to the shaft 202. Moving (actuating) the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the drive housing 208. In other embodiments, the power cable 214 may be omitted and electrical power may be supplied to the surgical tool 200 via an internal power source, such as one or more batteries or fuel cells. In such embodiments, the surgical tool 200 may alternatively be characterized and otherwise referred to as an "electrosurgical instrument" capable of providing electrical energy to the end effector 204. The power cable 214 may place the surgical tool 200 in communication with a generator 216 that supplies energy, such as electrical energy (e.g., radio frequency energy), ultrasonic energy, microwave energy, heat energy, or any combination thereof, to the surgical tool 200 and, more particularly, to the end effector 204.

Figure 4:
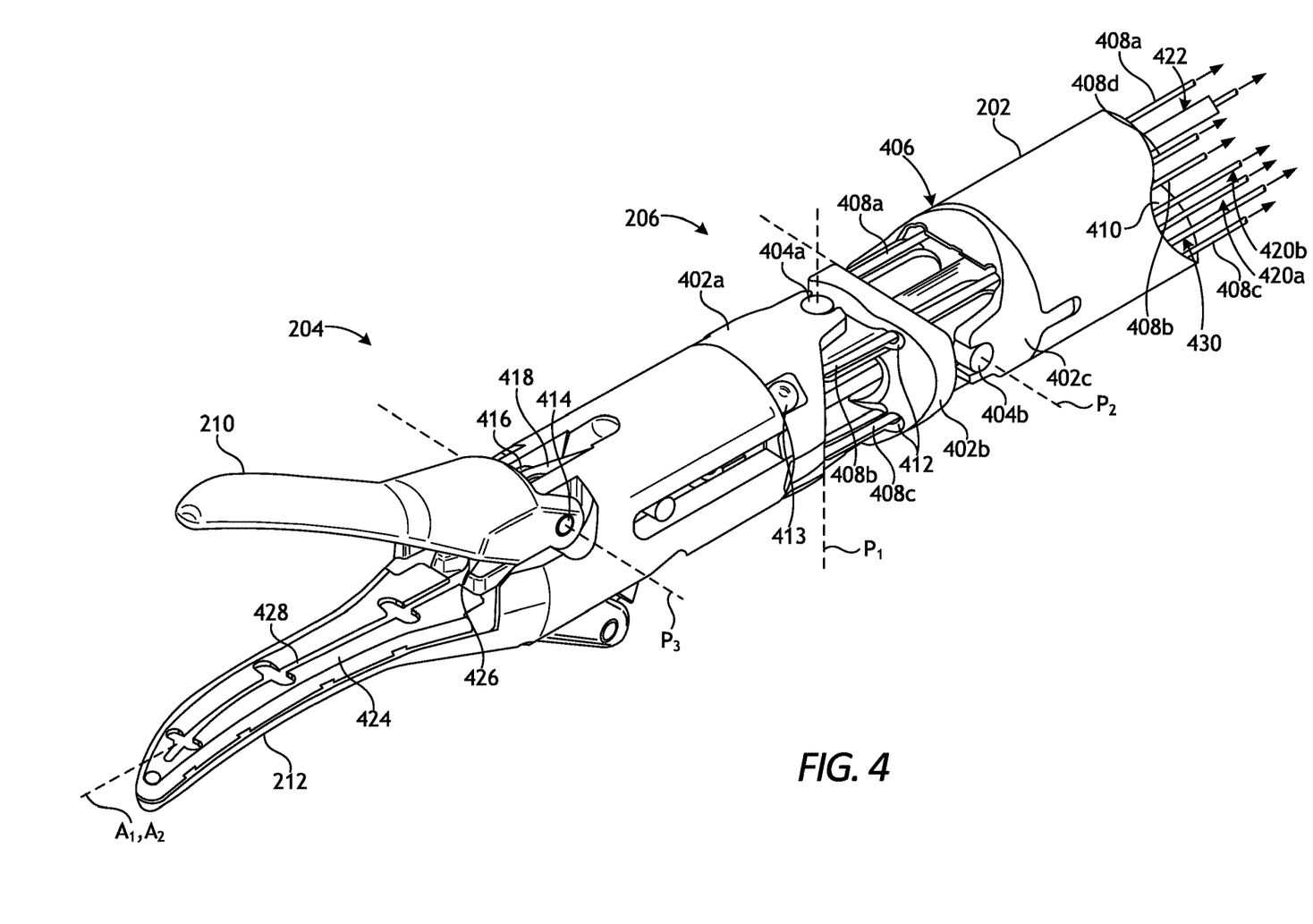
FIG. 4 is an enlarged isometric view of the distal end of the surgical tool of FIG. 2.

FIG. 4 is an enlarged isometric view of the distal end of the surgical tool 200 of FIG. 2. More specifically, FIG. 4 depicts an enlarged view of the end effector 204 and the wrist 206, with the jaws 210, 212 of the end effector 204 in the open position. The wrist 206 operatively couples the end effector 204 to the shaft 202. In some embodiments, however, a shaft adapter may be directly coupled to the wrist 206 and otherwise interpose the shaft 202 and the wrist 206. Accordingly, the wrist 206 may be operatively coupled to the shaft 202 either through a direct coupling engagement where the wrist 206 is directly coupled to the distal end of the shaft 202, or an indirect coupling engagement where a shaft adapter interposes the wrist 206 and the distal end of the shaft 202. As used herein, the term "operatively couple" refers to a direct or indirect coupling engagement between two components.

To operatively couple the end effector 204 to the shaft 202, the wrist 206 includes a first or "distal" linkage 402a, a second or "intermediate" linkage 402b, and a third or "proximal" linkage 402c. The linkages 402a-c facilitate articulation of the wrist 206 relative to the elongate shaft 202. Articulation via the linkages 402a-c may be limited to pitch only, yaw only, or a combination of pitch and yaw. As illustrated, the distal end of the distal linkage 402a may be coupled to the end effector 204 and, more particularly, to the lower jaw 212 (or an extension of the lower jaw 212). The proximal end of the distal linkage 402a may be rotatably coupled to the intermediate linkage 402b at a first axle 404a, and the intermediate linkage 402b may also be rotatably coupled to the proximal linkage 402c at a second axle 404b. The proximal end of the proximal linkage 402c may be coupled to a distal end 406 of the shaft 202 (or alternatively a shaft adapter).

A first pivot axis $P_1$ extends through the first axle 404a and a second pivot axis $P_2$ extends through the second axle 404b. The first pivot axis $P_1$ is substantially perpendicular (orthogonal) to the longitudinal axis $A_2$ of the end effector 204, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the wrist 206, and movement about the second pivot axis $P_2$ provides "pitch" articulation of the wrist 206. Alternatively, the first pivot axis $P_1$ could be configured to provide "pitch" articulation and the second pivot axis $P_2$ could be configured to provide "yaw" articulation.

A plurality of drive cables, shown as drive cables 408a, 408b, 408c, and 408d, extend longitudinally within a lumen 410 defined by the shaft 202 (or a shaft adaptor) and pass through the wrist 206 to be operatively coupled to the end effector 204. The drive cables 408a-d form part of the cable driven motion system briefly described above, and may be referred to and otherwise characterized as cables, bands, lines, cords, wires, woven wires, ropes, strings, twisted strings, elongate members, etc. The drive cables 408a-d can be made from a variety of materials including, but not limited to, metal (e.g., tungsten, stainless steel, etc.) a polymer (e.g., ultra-high molecular weight polyethylene), a synthetic fiber (e.g., KEVLAR®, VECTRAN®, etc.), or any combination thereof. While four drive cables 408a-d are depicted in FIG. 4, more or less than four drive cables 408a-d may be included, without departing from the scope of the disclosure.

The drive cables 408a-d extend proximally from the end effector 204 to the drive housing 208 (FIG. 2) where they are operatively coupled to various actuation mechanisms (e.g., capstans) or devices housed therein to facilitate longitudinal movement (translation) of the drive cables 408a-d within the lumen 410. Selective actuation of the drive cables 408a-d causes corresponding drive cables 408a-d to translate longitudinally within the lumen 410 and thereby cause pivoting movement (articulation) of the end effector 204. Moving a given drive cable 408a-d applies tension (i.e., pull force) to the given drive cable 408a-d in a proximal direction, which causes the given drive cable 408a-d to translate and thereby cause the end effector 204 to move (articulate).

The drive cables 408a-d each extend longitudinally through the first, second, and third linkages 402a-c. In some embodiments, each linkage 402a-c may define four, equidistantly-spaced apertures 412 (only two labeled) configured to guide the drive cables 408a-d through the wrist 206. The apertures 412 of each linkage 402a-c coaxially align when the end effector 204 is in the unarticulated position.

The distal end of each drive cable 408a-d may terminate at the distal linkage 402a, thus operatively coupling each drive cable 408a-d to the end effector 204 and, more particularly, to the lower jaw 212. The distal end of each drive cable 408a-d may be enlarged to facilitate fixed attachment thereof to the end effector 204. In some embodiments, as illustrated, the distal end of each drive cable 408a-d may include a ball crimp 413 (only one shown).

The jaws 210, 212 may be moved between the closed and open positions by pivoting the upper jaw 210 relative to the lower jaw 212. In the illustrated embodiment, the upper jaw 210 may be rotatably coupled (mounted) to the lower jaw 212 at a jaw axle 414. A third pivot axis $P_3$ extends through the jaw axle 414 and is generally perpendicular (orthogonal) to the first pivot axis $P_1$ and parallel to the second pivot axis $P_2$. In this embodiment, the lower jaw 212 remains stationary as the upper jaw 210 pivots about the third pivot axis $P_3$. In other embodiments, the end effector 204 may be designed such that the upper jaw 210 remains stationary as the lower jaw 212 pivots about the third pivot axis $P_3$, without departing from the scope of the disclosure.

A central pulley 416 (partially visible) may be mounted to the jaw axle 414 and receive a jaw cable 418 that may be actuated to selectively open and close the jaws 210, 212. Similar to the drive cables 408a-d, the jaw cable 418 extends longitudinally within the lumen 410 of the shaft 202 and passes through the wrist 206. The jaw cable 418 may form part of the cable driven motion system described herein and, therefore, may extend proximally from the end effector 204 to the drive housing 208 (FIG. 2). The jaw cable 418 may comprise a single line or wire looped around the central pulley 416 and opposing first and second ends 420a and 420b of the jaw cable 418 extend proximally to the drive housing 208. Actuation of corresponding drive inputs will cooperatively cause tension or slack in the jaw cable 418 and thereby cause the upper jaw 210 to rotate about the third pivot axis $P_3$ between the open and closed positions. More specifically, a tensile load assumed on the first end 420a of the jaw cable 418 may operate to close the jaws 210, 212, and a tensile load assumed on the second end 420b of the jaw cable 418 may operate to open the jaws 210, 212. Consequently, the first end 420a of the jaw cable 418 may alternately be referred to as the "closure cable" and the second end 420b of the jaw cable 418 may alternately be referred to as the "open cable."

In some embodiments, an electrical conductor 422 may supply electrical energy to the end effector 204 and, more particularly, to an electrode 424 included in the end effector 204. The electrical conductor 422 extends longitudinally within the lumen 410, through the wrist 206, and terminates at the electrode 424. In some embodiments, the electrical conductor 422 may comprise a wire, but may alternatively comprise a rigid or semi-rigid shaft, rod, or strip (ribbon) made of a conductive material. The electrode 424 may be partially covered with an insulative covering (overmold) made of a non-conductive material. Using the electrical conductor 422 and the electrode 424, the end effector 204 may be configured for monopolar or bipolar operation.

In the illustrated embodiment, the end effector 204 comprises a combination tissue grasper and vessel sealer that includes a cutting element 426 (mostly occluded), alternately referred to as a "knife" or "blade." The cutting element 426 is aligned with and configured to traverse a guide track 428 defined longitudinally in one or both of the upper and lower jaws 210, 212. The cutting element 426 may be operatively coupled to the distal end of a drive rod 430 that extends longitudinally within the lumen 410 and passes through the wrist 206. Longitudinal movement (translation) of the drive rod 430 correspondingly moves the cutting element 426 within the guide track(s) 428. Similar to the drive and jaw cables 408a-d, 418, the drive rod 430 may form part of the cable driven motion system and, therefore, may extend proximally from the cutting element 426 to the drive housing 208 (FIG. 2). Selective actuation of a corresponding drive input will cause the drive rod 430 to move distally or proximally within the lumen 410, and correspondingly move the cutting element 426 in the same direction.

Figure 5:
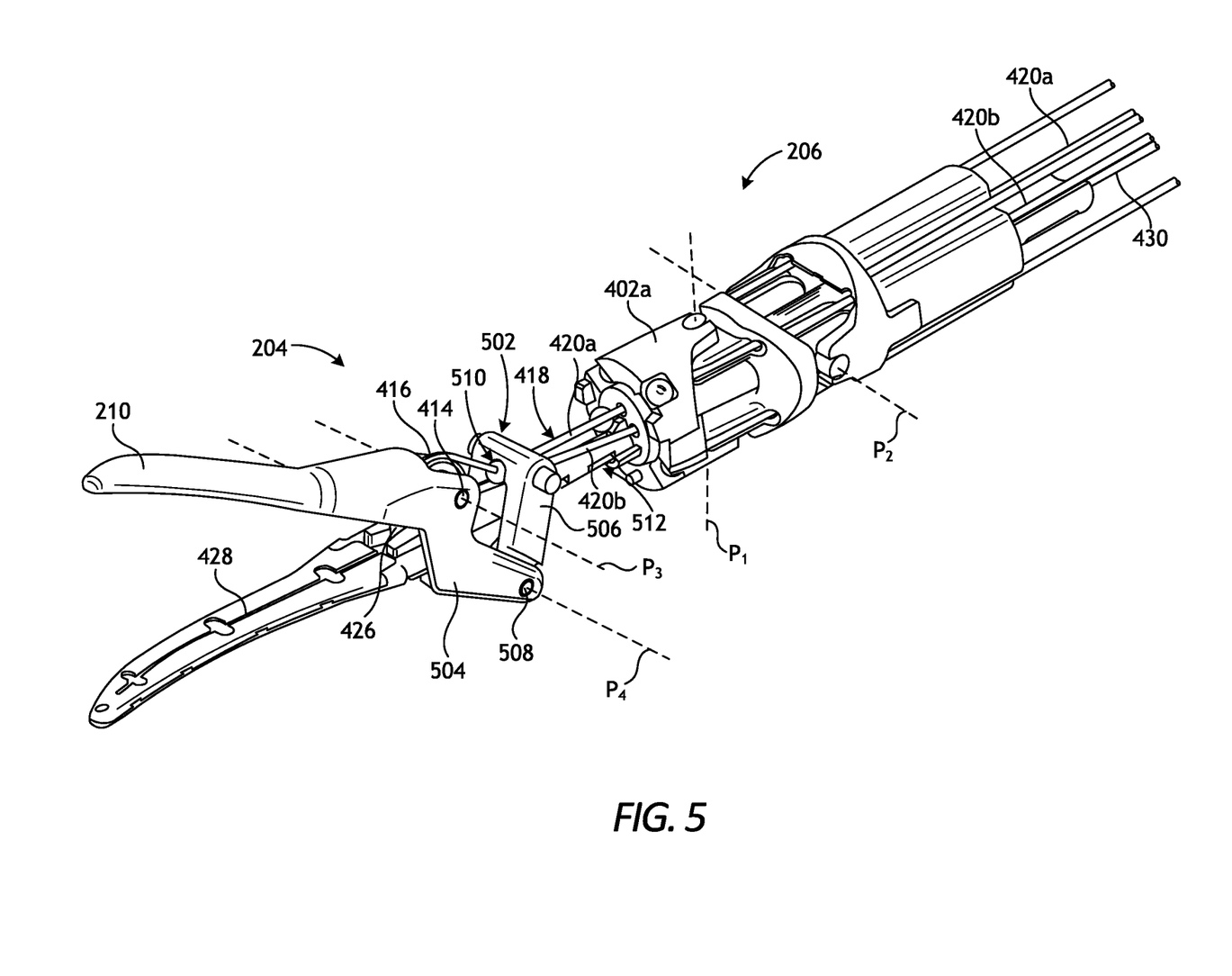
FIG. 5 is an isometric side view of the end effector of FIG. 4 in an open position (lower jaw omitted for clarity), according to one or more embodiments.

FIG. 5 is an isometric side view of the end effector 204 in an open position, according to one or more embodiments. More particularly, FIG. 5 depicts the upper jaw 210 pivoted to the open position, and the lower jaw 212 (FIG. 4) is omitted to enable viewing of the internal components of the end effector 204. As illustrated, the end effector 204 includes a pivot link 502 operatively coupled to the upper jaw 210. More specifically, the upper jaw 210 provides or otherwise defines one or more legs 504 (one shown, one occluded) that are pivotably coupled to a corresponding one or more legs 506 (one shown, one occluded) of the pivot link 502 at a pivot axle 508. A fourth pivot axis $P_4$ extends through the pivot axle 508 and may be generally perpendicular (orthogonal) to the first pivot axis $P_1$ and parallel to the second and third pivot axes $P_2$, $P_3$.

The central pulley 416 (mostly occluded) is rotatably supported on the jaw axle 414, and the jaw cable 418 loops around the central pulley 416 and the opposing ends 420a,b of the jaw cable 418 extend proximally through the wrist 206. The jaw cable 418 may be operatively coupled to the pivot link 502 such that movement (i.e., longitudinal translation) of the jaw cable 418 correspondingly moves the pivot link 502. For example, a cable anchor 510 may be secured to or otherwise form part of one proximally extending end 420a,b of the jaw cable 418 and may help operatively couple the jaw cable 418 to the pivot link 502.

To move the jaws 210, 212 to the open position, the jaw cable 418 may be actuated to move the pivot link 502 distally, which may be done, for example, by pulling proximally on the second end 420b of the jaw cable 418 (i.e., the "open cable"). As the pivot link 502 moves distally, the legs 506 of the pivot link 502 act on the legs 504 of the upper jaw 210 at the pivot axle 508 and forces the legs 504 downward in rotation about the fourth pivot axis $P_4$. Downward movement of the legs 504 correspondingly causes the upper jaw 210 to pivot about the third pivot axis $P_3$. As it pivots about the third pivot axis $P_3$, the upper jaw 210 is moved to the open position.

To move the upper jaw 210 back to the closed position, the jaw cable 418 may be actuated to move the pivot link 502 proximally, which may be done by pulling proximally on the first end 420a of the jaw cable 418 (i.e., the "closure cable"). This causes the pivot link 502 to pull upward on the legs 504 of the upper jaw 210 in rotation about the fourth pivot axis $P_4$, and upward movement of the legs 504 correspondingly causes the upper jaw 210 to pivot about the third pivot axis $P_3$ and moves the upper jaw 210 to the closed position.

Figure 6A:
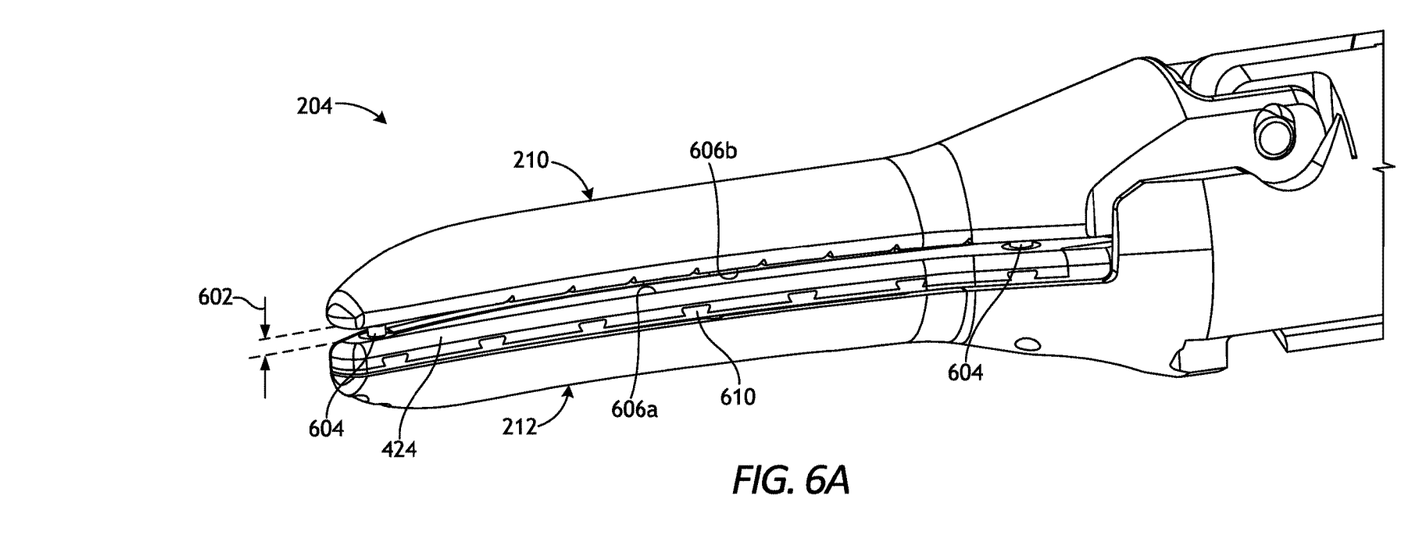
FIGS. 6A and 6B are enlarged isometric and cross-sectional views, respectively, of the end effector of FIGS. 2, 4, and 5, according to one or more embodiments of the disclosure.
Figure 6B:
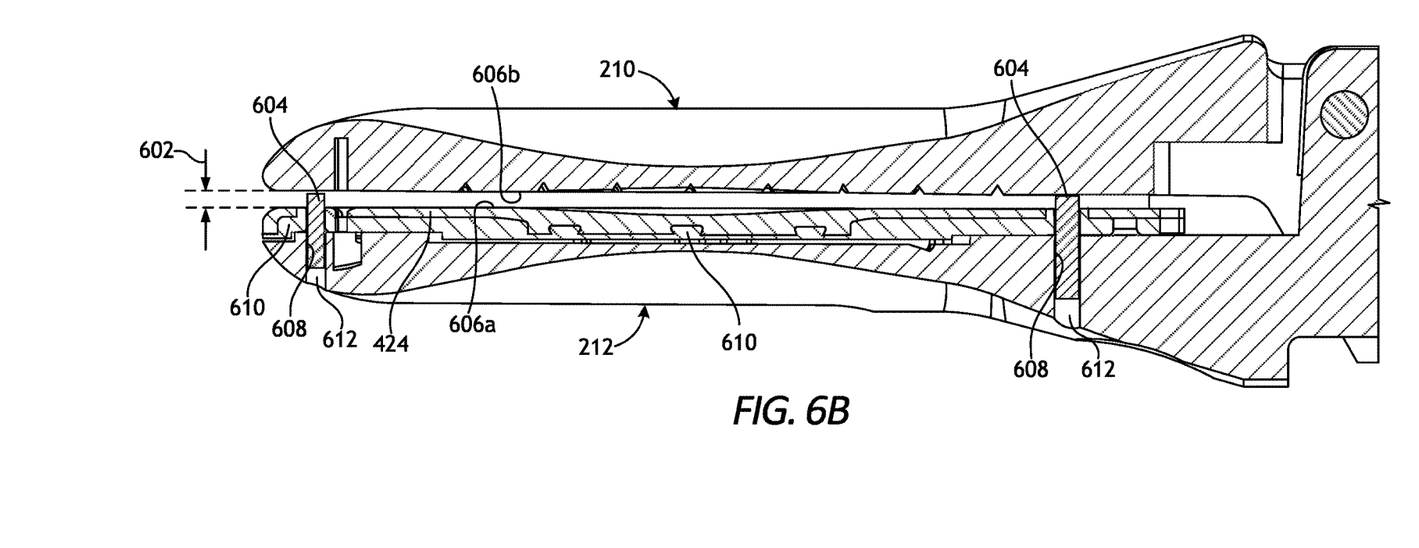

FIGS. 6A and 6B are enlarged isometric and cross-sectional side views, respectively, of the end effector 204, according to one or more embodiments. The jaws 210, 212 are depicted in the closed position and slightly offset from each other such that a jaw gap 602 is defined between the inner (opposing) surfaces of each jaw 210, 212. Jaw gap 602 is generally uniform such that the inner surfaces of each jaw 210, 212 are parallel to one another. However, in some cases the jaw gap 602 may be non-uniform to enhance sealing performance by creating different gap zones across the opposing surfaces that can accommodate differences in tissue types or thicknesses, said gap zones remaining within the overall specified range of jaw gap 602. The jaw gap 602 is critical to the effective operation of the end effector 204 in creating proper tissue seals. For instance, the magnitude of the jaw gap 602 can be tied to a predetermined manufacturing specification, such as 0.005 in If the jaw gap 602 exceeds the predetermined value by just a few thousands of an inch (in either direction), the jaws 210, 212 may be incapable of properly sealing cut tissue. In such cases, the end effector 204 may be unfit for its intended purpose and may be scrapped at a total loss. The systems and methods described herein compensate for tolerance variation of the individual components that make up the end effector 204, or any other end effector assembly.

The jaw gap 602 will be typically set during manufacture and assembly of the end effector 204 and must take into account manufacturing tolerances inherent in the individual component parts of the end effector 204. According to embodiments of the present disclosure, the jaw gap 602 may be accurately set during manufacture and assembly of the end effector 204 by using one or more spacer pins 604

(alternately referred to as "jaw gap setting pins") secured to the lower jaw 212. While two spacer pins 604 are visible in FIGS. 6A-6B, more or less than two may be employed, without departing from the scope of the disclosure. It is noted that the systems, methods and embodiments described herein are applicable not only to setting the jaw gap 602 of the end effector 204 shown in FIGS. 6A-6B. Rather, the systems, methods and embodiments described herein may be equally applicable to setting jaw gap of any end effector that includes opposing jaws, without departing from the scope of the disclosure.

In the illustrated embodiment, the spacer pins 604 may extend (protrude) past an upper surface 606a of the lower jaw 212 to engage an opposing lower surface 606b of the upper jaw 210 when the upper jaw 210 is moved to the closed position. The distance each spacer pin 604 extends past the upper surface 606a may be substantially similar to the magnitude of the jaw gap 602. The spacer pins 604 may prevent the upper jaw 210 from exceeding (moving past) the jaw gap 602 upon closing, thus ensuring that the jaw gap 602 stays consistent during operation of the end effector 204. Moreover, during operation, the exposed top of each spacer pin 604 may act like teeth helpful in retaining grasped tissue.

In some embodiments, each spacer pin 604 may be received within a corresponding aperture 608 defined in the lower jaw 212. In some embodiments, as illustrated, the aperture 608 may be cooperatively defined by the lower jaw 212 and an overmold 610 (insulative covering) that partially covers the electrode 424. In other embodiments, however, the aperture 608 may be cooperatively defined by the lower jaw 212, the electrode 424, and the overmold 610, without departing from the scope of the disclosure. Once set in the corresponding aperture 608 to the proper height for the resulting jaw gap 602, as will be described below, the spacer pins 604 may be secured to the lower jaw 212. An open orifice 612 at the bottom of each aperture 608, for instance, may provide access to the bottom of the spacer pins 604 to secure the spacer pins 604 to the lower jaw 212 using any suitable attachment means. Example attachment means include, but are not limited to, welding (e.g., spot, laser, sonic, ultrasonic, etc.), an adhesive, an interference fit (e.g., variable size or dissimilar shaped pin 604 and aperture 608), a shrink fit, a material deformation fit (e.g., similar to the setting of a rivet), or any combination thereof.

The spacer pin(s) 604 may be made of any rigid or semi-rigid material including, but not limited to, a metal, a plastic, a rubber or an elastomer, a composite material, or any combination thereof. In some embodiments, the spacer pin(s) 604 may be made of a conductive material including, but not limited to, stainless steel, plated steel, copper, gold, aluminum, platinum, tungsten, silver, nickel, beryllium, rhodium, magnesium, iridium, tin, chromium, cobalt, and alloys thereof, or any combination thereof. In such embodiments, the spacer pin(s) 604 may be welded to and form an integral part of the lower jaw 212 to provide a ground path during operation of the end effector 204.

It is noted that embodiments are contemplated herein where the spacer pin(s) 604 are alternatively secured to the upper jaw 210. In such embodiments, the lower jaw 212 may instead be movable relative to the upper jaw 210, which remains stationary, and the spacer pin(s) 604 may prevent the lower jaw 212 from exceeding (moving past) the jaw gap 602 upon closing. Moreover, the gap setting concepts contemplated herein are also applicable to embodiments where the upper and lower jaws 210, 212 are each movable relative to each other (bi-lateral jaw motion).

Figure 7A:
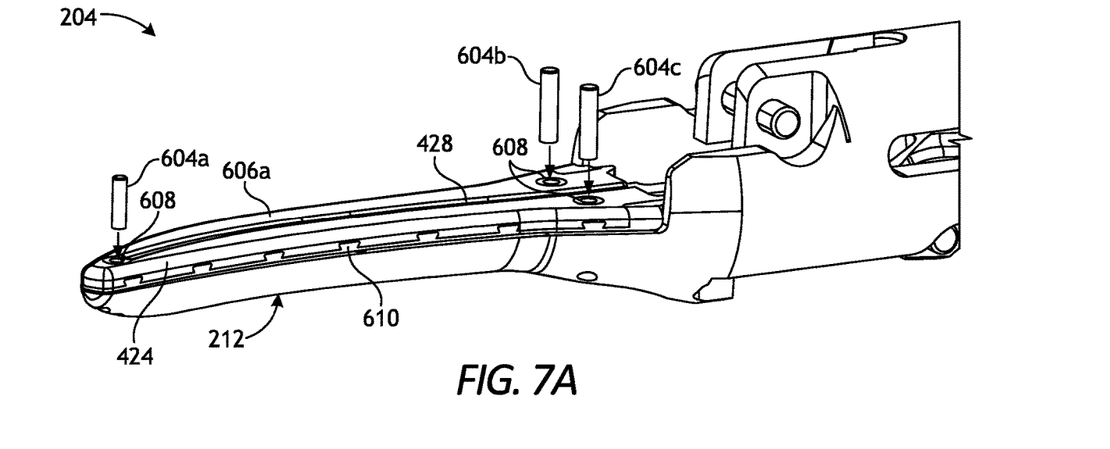
FIGS. 7A-7C depict progressive assembly views of the end effector and example setting of the jaw gap of FIGS. 6A-6B, according to one or more embodiments.
Figure 7B:
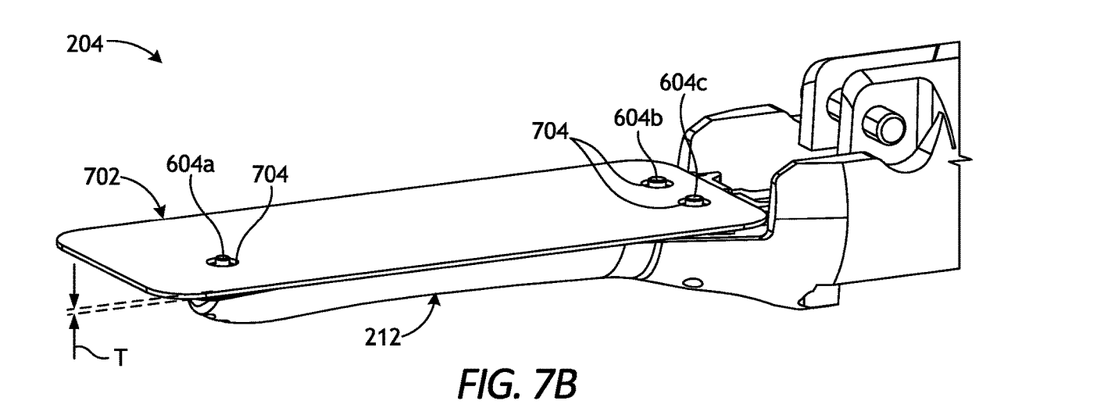
Figure 7C:
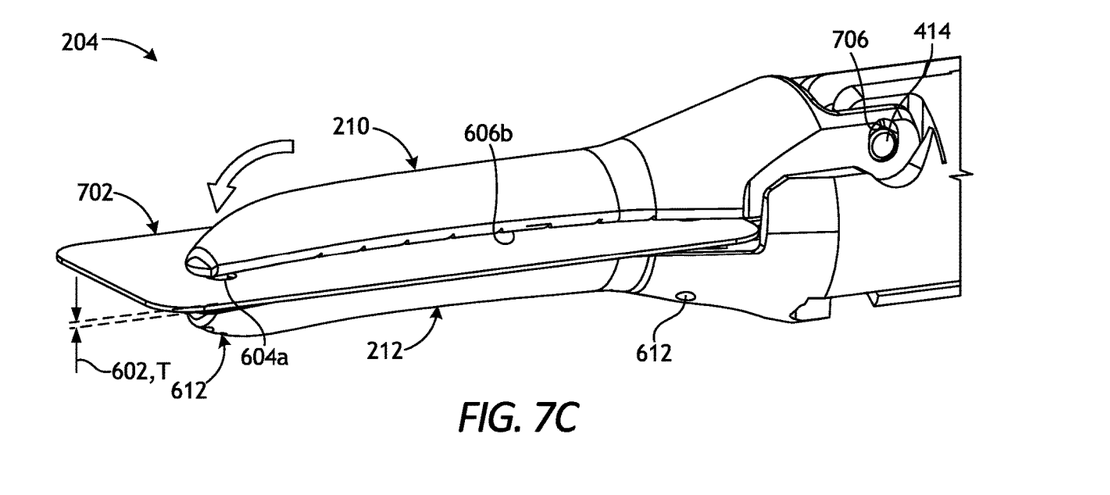

FIGS. 7A-7C depict progressive assembly views of the end effector 204 and example setting of the jaw gap 602, according to one or more embodiments. In FIG. 7A, the lower jaw 212 is depicted and includes the electrode 424 and the overmold 610 covering a portion of the electrode 424 and defining the upper surface 606a of the lower jaw 212. In at least one embodiment, the overmold 610 may be made of a non-conductive material, such as a polymer. The guide track 428 is defined in the overmold 610 and extends longitudinally along a portion of the lower jaw 212 to receive the cutting element 426 (FIG. 4) as it is axially extended for cutting.

In the illustrated embodiment, the end effector 204 includes three spacer pins, shown as a distal spacer pin 604a and first and second proximal spacer pins 604b, 604c. The distal spacer pin 604a may be arranged near the distal end (tip) of the lower jaw 212, and the proximal spacer pins 604b,c may be arranged on opposite sides of the guide track 428 near the proximal end of the lower jaw 212. As illustrated, the spacer pins 604a-c may each comprise generally cylindrical structures receivable within a corresponding aperture 608 defined in the lower jaw 212 and, more particularly, cooperatively defined by the overmold 610 and the underlying electrode 424.

In some embodiments, each of the spacer pins 604a-c may be the same size and exhibit the same cross-sectional shape. In other embodiments, however, one or more of the spacer pins 604a-c may be sized differently or exhibit a cross-sectional shape different than the other spacer pin(s) 604a-c. In the illustrated embodiment, for example the proximal spacer pins 60b,c are larger and longer than the distal spacer pin 604a.

The apertures 608 may be sized and shaped to receive the corresponding spacer pins 604a-c. In some embodiments, the apertures 608 may be sized to receive the corresponding spacer pins 604a-c via an interference fit. In one or more embodiments, for example, the portion of the aperture 608 defined by the overmold 610 may be sized to provide an interference fit. In other embodiments, however, the portion of the aperture 608 defined by the electrode 424 may be sized to provide an interference fit. In yet other embodiments, portions of the aperture 608 defined by both the overmold 610 and the electrode 424 may be sized to provide an interference fit, without departing from the scope of the disclosure. Receiving the spacer pins 604a-c within the apertures 608 via an interference fit allows the spacer pins 604a-c to be pressed into the corresponding apertures 608 to a desired depth to achieve the jaw gap 602 (FIG. 7C).

In FIG. 7B, a shim 702 may be positioned on the upper surface 606a (FIG. 7A) of the lower jaw 212. The shim 702 may have a uniform depth or thickness T that is substantially similar to the magnitude of the jaw gap 602 (FIG. 7C). Consequently, the shim 702 may be used as a gauge to accurately set the jaw gap 602, as discussed below.

In some embodiments, as illustrated, the shim 702 may comprise a plate-like structure. In other embodiments, however, the shim 702 may comprise or otherwise provide one or more elongate rods having the thickness T, without departing from the scope of the disclosure. In yet other embodiments, the shim 702 may comprise any rigid or semi-rigid structure manufactured with sufficiently small tolerances to set the proper jaw gap 602. If a non-uniform jaw gap is desired as discussed above, the shim may be constructed of progressively increasing (or decreasing) thicknesses $T_2$, $T_3$, $T_4$, etc. to achieve the desired final (target) jaw gap. In the illustrated embodiment, the plate-like shim 702 defines holes 704 alignable with the apertures 608

(FIG. 7A) to accommodate the spacer pins 604a-c. The spacer pins 604a-c may be received within the corresponding apertures 608 before or after positioning the shim 702 on the lower jaw 212 and aligning the holes 704 with the apertures 608.

In FIG. 7C, the upper jaw 210 is assembled to the lower jaw 212 at the jaw axle 414. To set the spacer pins 604a-c (mostly occluded) to the proper height, the upper jaw 210 may be pivoted toward the closed position until the lower surface 606b of the upper jaw 210 engages (rests against) the shim 702. As the upper jaw 210 moves toward the closed position, the lower surface 606b will engage and press the spacer pins 604a-c deeper into the corresponding apertures 608 (FIG. 7A) until the lower surface 606b engages the shim 702 and stops any further advancement of the spacer pins 604a-c. Because the thickness T of the shim 702 is substantially similar to the magnitude of the jaw gap 602, the resulting height of the spacer pins 604a-c extending past (protruding from) the upper surface 606a (FIG. 7A) of the lower jaw 212 will also be substantially similar to the jaw gap 602.

Once the spacer pins 604a-c are set in the corresponding apertures 608 (FIG. 7A) to the proper height for the jaw gap 602, the spacer pins 604a-c may be secured to the lower jaw 212, as generally described above. The open orifice 612 at the bottom of each aperture 608 provides access to the bottom of the spacer pins 604a-c to secure the spacer pins 604a-c to the lower jaw 212 using any of the attachment means mentioned herein.

Once the spacer pins 604a-c are secured to the lower jaw 212, the upper jaw 210 may then be secured to the jaw axle 414. As illustrated, instead of a round hole, the upper jaw 210 may define an elongated slot 706 that receives the jaw axle 414. The elongated slot 706 allows the upper jaw 210 to be adjustable while setting the jaw gap 602 to accommodate manufacturing variances of the end effector 204 that may be prevalent. Once the spacer pins 604a-c are set and secured to the lower jaw 212, the position of the upper jaw 210 may be set by securing the upper jaw 210 to the jaw axle 414 at the elongated slot 706. Example attachment means include, but are not limited to, welding (e.g., spot, laser, sonic, ultrasonic, etc.), an adhesive, or any combination thereof.

Accordingly, the upper jaw 210 may be constrained at two separate locations, i.e., at the spacer pin(s) 604a-c and the jaw axle 414, thus providing a consistent jaw gap 602 spacing each time the jaws 210, 212 move to the closed position. As will be appreciated, the foregoing assembly method combats part variation and tolerance accumulation throughout the assembly of the end effector 204, and may be used on any type of end effector having opposing jaws to help compensate for manufacturing variations in the individual component parts of the jaws.

Still referring to FIGS. 7A-7B, in an alternative embodiment, the apertures 608 may have a large clearance for the corresponding spacer pins 604a-c, thus resulting in a free fit. In such embodiments, with the shim 702 in place and the upper jaw 210 moved to the closed position, the end effector 204 may be turned upside down and the spacer pins 604a-c may be dropped into the corresponding apertures 608. Under the force of gravity, the spacer pins 604a-c will advance within the corresponding apertures 608 until engaging the lower surface 606b of the upper jaw 210. The spacer pins 604a-c may then be secured to the lower jaw 212 via the corresponding open orifice 612 at the bottom of each aperture 608, and the upper jaw 210 may be secured to the jaw axle 414 at the elongated slot 706, as generally described above.

Embodiments disclosed herein include:

A. An end effector for a surgical tool that includes a first jaw that defines an aperture, a second jaw rotatably coupled to the first jaw, and a spacer pin received within the aperture and protruding from an upper surface of the first jaw, wherein the spacer pin is adjustable within the aperture to define a jaw gap between the first and second jaws when the second jaw is moved to a closed position and engages the spacer pin, and wherein the spacer pin is secured within the aperture to set the jaw gap.

B. A method of setting a jaw gap of an end effector includes receiving a spacer pin within an aperture defined in a first jaw of the end effector, the spacer pin protruding from an upper surface of the first jaw, rotatably coupling a second jaw to the first jaw, pivoting the second jaw toward a closed position and thereby pressing the spacer pin into the aperture with the second jaw to define the jaw gap, and securing the spacer pin within the aperture to set the jaw gap.

C. A method of setting a jaw gap of an end effector includes positioning a shim on an upper surface of a first jaw, the shim having a thickness corresponding to the jaw gap, rotatably coupling a second jaw to the first jaw and pivoting the second jaw to a closed position where the second jaw engages the shim, dropping a spacer pin into the aperture and advancing the spacer pin until the spacer pin engages the second jaw, and securing the spacer pin within the aperture.

Each of embodiments A, B, and C may have one or more of the following additional elements in any combination: Element 1: wherein the spacer pin is secured to the first jaw using an attachment means selected from the group consisting of welding, an adhesive, an interference fit, a shrink fit, a material deformation fit, and any combination thereof. Element 2: wherein the first jaw includes an electrode and an overmold that partially covers the electrode, and wherein the aperture is cooperatively defined by the first jaw and one or both of the electrode and the overmold. Element 3: wherein the aperture is cooperatively defined by the first jaw and the overmold, and wherein the spacer pin is made of a conductive material and is secured to the first jaw within the aperture. Element 4: wherein the aperture is cooperatively defined by the first jaw, the electrode, and the overmold, and wherein the spacer pin is made of a non-conductive material and is secured to the first jaw within the aperture. Element 5: wherein the spacer pin is received within the aperture via an interference fit against at least one of the overmold and the electrode. Element 6: wherein the aperture is a first aperture located near a distal end of the first jaw and the spacer pin is a first spacer pin, the end effector further comprising a second spacer pin received within a second aperture defined in the first jaw near a proximal end of the first jaw and protruding from the upper surface of the first jaw, and wherein the jaw gap is defined between the first and second jaws when the second jaw is moved to the closed position and engages the first and second spacer pins. Element 7: wherein the first and second spacer pins are dissimilar in size. Element 8: further comprising a third spacer pin received within a third aperture defined in the first jaw near the proximal end of the first jaw and protruding from the upper surface of the first jaw, wherein the second and third spacer pins are arranged on opposing sides of a guide track longitudinally defined in the first jaw, and wherein the jaw gap is defined between the first and second jaws when the second jaw is moved to the closed position and engages the first, second, and third spacer pins. Element 9: wherein the second jaw is rotatably coupled to the first jaw at a jaw axle extending through an elongated slot defined on the second jaw, and wherein the second jaw is secured to the jaw axle at the elongated slot. Element 10: wherein the jaw gap is uniform between the first and second jaws. Element 11: wherein the jaw gap is non-uniform between the first and second jaws.

Element 12: further comprising positioning a shim on the upper surface of the first jaw, the shim having a thickness corresponding to the jaw gap, and stopping the second jaw from advancing the spacer pin into the aperture once the second jaw engages the shim. Element 13: wherein positioning the shim on the upper surface of the first jaw precedes receiving the spacer pin within the aperture. Element 14: wherein rotatably coupling the second jaw to the first jaw comprises extending a jaw axle through an elongated slot defined on the second jaw, and securing the second jaw to the jaw axle at the elongated slot once the second jaw pivots to the closed position. Element 15: wherein the first jaw comprises an electrode and an overmold that partially covers the electrode and the aperture is cooperatively defined by the electrode and the overmold, and wherein securing the spacer pin to the first jaw comprises welding the spacer pin to the first jaw. Element 16: further comprising receiving the spacer pin within the aperture via an interference fit against at least one of the overmold and the electrode. Element 17: wherein the aperture is a first aperture located near a distal end of the first jaw and the spacer pin is a first spacer pin, the method further comprising receiving a second spacer pin within a second aperture defined in the first jaw near a proximal end of the first jaw and protruding from the upper surface of the first jaw, pivoting the second jaw toward the closed position and thereby pressing the first and second spacer pins into the first and second apertures, respectively, with the second jaw to define the jaw gap, and securing the first and second spacer pins within the first and second apertures, respectively, to set the jaw gap. Element 18: further comprising receiving a third spacer pin within a third aperture defined in the first jaw near the proximal end of the first jaw and protruding from the upper surface of the first jaw, wherein the second and third spacer pins are arranged on opposing sides of a guide track longitudinally defined in the first jaw.

Element 19: wherein rotatably coupling the second jaw to the first jaw comprises extending a jaw axle through an elongated slot defined on the second jaw, and securing the second jaw to the jaw axle at the elongated slot once the second jaw pivots to the closed position. Element 20: wherein the first jaw comprises an electrode and an overmold that partially covers the electrode and the aperture is cooperatively defined by the electrode and the overmold, and wherein securing the spacer pin to the first jaw comprises welding the spacer pin to the first jaw.

By way of non-limiting example, exemplary combinations applicable to A, B, and C include: Element 2 with Element 3; Element 2 with Element 4; Element 2 with Element 5; Element 6 with Element 7; Element 6 with Element 8; Element 12 with Element 13; Element 15 with Element 16; and Element 17 with Element 18.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An end effector for a surgical tool, comprising:
   a first jaw that defines an aperture extending through the first jaw and terminating at an open orifice on an opposing side of the first jaw;
   a second jaw rotatably coupled to the first jaw; and
   a spacer pin received within the aperture and protruding from an upper surface of the first jaw,
   wherein moving the second jaw to a closed position engages the spacer pin and adjusts a position of the spacer pin within the aperture to define a jaw gap between the first and second jaws, and
   wherein the jaw gap is set by securing the spacer pin within the aperture via the open orifice.

2. The end effector of claim 1, wherein the spacer pin is secured to the first jaw using an attachment means selected from a group consisting of welding, an adhesive, an interference fit, a shrink fit, a material deformation fit, and any combination thereof.

3. The end effector of claim 1, wherein the first jaw includes an electrode and an overmold that partially covers the electrode, and wherein the aperture is cooperatively defined by the first jaw and one or both of the electrode and the overmold.

4. The end effector of claim 3, wherein the aperture is cooperatively defined by the first jaw and the overmold, and wherein the spacer pin is made of a conductive material and is secured to the first jaw within the aperture.

5. The end effector of claim 3, wherein the aperture is cooperatively defined by the first jaw, the electrode, and the overmold, and wherein the spacer pin is made of a non-conductive material and is secured to the first jaw within the aperture.

6. The end effector of claim 3, wherein the spacer pin is received within the aperture via an interference fit against at least one of the overmold and the electrode.

7. The end effector of claim 1, wherein the aperture is a first aperture located near a distal end of the first jaw and the spacer pin is a first spacer pin, the end effector further comprising:
   a second spacer pin received within a second aperture defined in the first jaw near a proximal end of the first jaw and protruding from the upper surface of the first jaw, and
   wherein the jaw gap is defined between the first and second jaws when the second jaw is moved to the closed position and engages the first and second spacer pins.

8. The end effector of claim 7, wherein the first and second spacer pins are dissimilar in size.

9. The end effector of claim 7, further comprising:
   a third spacer pin received within a third aperture defined in the first jaw near the proximal end of the first jaw and protruding from the upper surface of the first jaw,
   wherein the second and third spacer pins are arranged on opposing sides of a guide track longitudinally defined in the first jaw, and
   wherein the jaw gap is defined between the first and second jaws when the second jaw is moved to the closed position and engages the first, second, and third spacer pins.

10. The end effector of claim 1, wherein the second jaw is rotatably coupled to the first jaw at a jaw axle extending through an elongated slot defined on the second jaw, and wherein the second jaw is secured to the jaw axle at the elongated slot.

11. The end effector of claim 1, wherein the jaw gap is uniform between the first and second jaws.

12. The end effector of claim 1, wherein the jaw gap is non-uniform between the first and second jaws.

13. A method of setting the jaw gap of the end effector of claim 1, comprising:
   receiving the spacer pin within the aperture defined in the first jaw of the end effector, the spacer pin protruding from the upper surface of the first jaw and the aperture extending through the first jaw and terminating at the open orifice on the opposing side of the first jaw;
   rotatably coupling the second jaw to the first jaw;
   pivoting the second jaw toward the closed position and thereby pressing the spacer pin into the aperture with the second jaw to define the jaw gap; and
   setting the jaw gap by securing the spacer pin within the aperture via the open orifice.

14. The method of claim 13, further comprising:
   positioning a shim on the upper surface of the first jaw, the shim having a thickness corresponding to the jaw gap; and
   stopping the second jaw from advancing the spacer pin into the aperture once the second jaw engages the shim.

15. The method of claim 14, wherein positioning the shim on the upper surface of the first jaw precedes receiving the spacer pin within the aperture.

16. The method of claim 13, wherein rotatably coupling the second jaw to the first jaw comprises:
   extending a jaw axle through an elongated slot defined on the second jaw; and
   securing the second jaw to the jaw axle at the elongated slot once the second jaw pivots to the closed position.

17. The method of claim 13, wherein the first jaw comprises an electrode and an overmold that partially covers the electrode and the aperture is cooperatively defined by the electrode and the overmold, and wherein securing the spacer pin to the first jaw comprises welding the spacer pin to the first jaw via the open orifice.

18. The method of claim 17, further comprising receiving the spacer pin within the aperture via an interference fit against at least one of the overmold and the electrode.

19. The method of claim 13, wherein the aperture is a first aperture located near a distal end of the first jaw, the spacer pin is a first spacer pin, and the open orifice is a first open orifice, the method further comprising:
   receiving a second spacer pin within a second aperture defined in the first jaw near a proximal end of the first jaw and protruding from the upper surface of the first jaw, the second aperture extending through the first jaw and terminating at a second open orifice on the opposing side of the first jaw;
   pivoting the second jaw toward the closed position and thereby pressing the first and second spacer pins into the first and second apertures, respectively, with the second jaw to define the jaw gap; and
   setting the jaw gap by securing the first and second spacer pins within the first and second apertures via the first and second open orifices, respectively.

20. The method of claim 19, further comprising receiving a third spacer pin within a third aperture defined in the first jaw near the proximal end of the first jaw and protruding from the upper surface of the first jaw, wherein the third aperture extends through the first jaw and terminates at a third open orifice on the opposing side of the first jaw, and wherein the second and third spacer pins are arranged on opposing sides of a guide track longitudinally defined in the first jaw.

21. A method of setting the jaw gap of the end effector of claim 1, comprising:
   positioning a shim on the upper surface of the first jaw, the shim having a thickness corresponding to the jaw gap;
   rotatably coupling the second jaw to the first jaw and pivoting the second jaw to the closed position where the second jaw engages the shim;
   dropping the spacer pin into the aperture defined in the first jaw via the open orifice and advancing the spacer pin until the spacer pin engages the second jaw; and
   securing the spacer pin within the aperture via the open orifice.

22. The method of claim 21, wherein rotatably coupling the second jaw to the first jaw comprises:
   extending a jaw axle through an elongated slot defined on the second jaw; and
   securing the second jaw to the jaw axle at the elongated slot once the second jaw pivots to the closed position.

23. The method of claim 21, wherein the first jaw comprises an electrode and an overmold that partially covers the electrode and the aperture is cooperatively defined by the electrode and the overmold, and wherein securing the spacer pin to the first jaw comprises welding the spacer pin to the first jaw.

* * * * *